(12) United States Patent
Broglie et al.

(10) Patent No.: US 6,930,226 B2
(45) Date of Patent: Aug. 16, 2005

(54) GRANULE-BOUND STARCH SYNTHASE

(75) Inventors: Karen E. Broglie, Landenberg, PA (US); Karlene H. Butler, Newark, DE (US); Leslie T. Harvell, Newark, DE (US); Jonathan E. Lightner, Mulino, OR (US); Emil M. Orozco, Jr., Cochranville, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 115 days.

(21) Appl. No.: 10/138,075

(22) Filed: May 2, 2002

(65) Prior Publication Data

US 2003/0087369 A1 May 8, 2003

Related U.S. Application Data

(60) Provisional application No. 60/288,315, filed on May 3, 2001.

(51) Int. Cl.[7] .................. C12N 15/82; C12N 15/29; A01H 5/00; A01H 5/10; C12P 19/04
(52) U.S. Cl. .................. 800/284; 800/278; 800/286; 435/69.1; 435/101; 435/320.1; 435/419; 435/468; 536/23.2; 536/23.6; 536/24.5
(58) Field of Search ............................ 800/278, 284, 800/286; 435/69.1, 101, 320.1, 419, 468; 536/23.2, 23.6, 24.5

(56) References Cited

U.S. PATENT DOCUMENTS 6,130,367 A    10/2000  Kossmann et al.
6,307,125 B1 * 10/2001  Block et al. ............... 800/284

FOREIGN PATENT DOCUMENTS

WO    WO 92/11376    7/1992

OTHER PUBLICATIONS

Nakamura et al. GenBank Accession No. Q9SQ58 published May 1, 2000.*
Toshiki Nakamura et al., Plant Physiol., vol. 118:451–459, 1996, Characterization of a Granule–Bound Starch Synthase Isoform Found in the Pericarp of Wheat.
Gerhard P. Schwall et. al., Nature Biotechnology, vol. 18:551–554, 2000, Production of Very–High–Amylose Potato Starch by Inhibition of SBE A and B.
Feike R. Van Der Leij et. al., Mol. Gen. Genet., vol. 228:240–248, 1991, Sequence of the Structural Gene for Granule–Bound Starch Synthase of Potato (Solanum Tubcrosum) and Evidence for a Single Point Deletion in the ANF Allele.
National Center for Biotechnology Information General Identifier No. 6136121, Jun. 15, 2002, Merida, A. et. al., Expression of the Granule–Bound Starch Synthase I (WAXY) Gene from Snapdragon is Developmentally and Circadian Clock Regulated.
Angel Merida et. al., Plant Physiology, vol. 120:401–409, 1999, Expression of the Granule–Bound Starch Synthase I (WAXY) Gene from Snapdragon is Developmentally and Circadian Clock Regulated.
National Center for Biotechnology Information General Identifer No. 6492245, Dec. 1, 1999, Nakamura, T. et. al.
Patricia L. Vrinten et. al., Plant Physiology, vol. 122:255–263, 2000, Wheat Granule–Bound Starch Synthase I and II Are Encoded by Separate Genes That Are Expressed in Different Tissues.
National Center for Biotechnology Information General Identifier No. 15626365, Accession No: CAC69955, Sep. 16, 2001, A. Edwards et al., Discrete Forms of Amylose Are Synthesized by Isoforms of GBSSI in Pea.
Koji Furukawa et. al., The Journal of Biological Chemistry, vol. 265:2086–2090, 1990, Identification of Lysine 15 at the Active Site in *Escherichia Coli* Glycogen Synthase.
Koji Furukawa et. al., The Journal of Biological Chemistry. vol. 268:23837–23842, 1993, Role of the Conserved Lys–X–Gly–Gly Sequence at the ADP–Glucose–Binding Site in *Escherichia Coli* Glycogen Synthase.
M. Yamamori et. al., Euphytica, vol. 64:215–219, 1992, Variations in the Content of Starch–Granule Bound Protein Amoung Several Japanese Cultivars of Common Wheat (Triticum Aestivum L.).
George W. Singletary et. al., Plant Physiol., vol. 113:293–304, 1997, Influence of Gene Dosage on Carbohydrate Synthesis and Enzymatic Activities in Endosperm of Starch–Deficient Mutants PF Maize.

* cited by examiner

Primary Examiner—David T. Fox

(57) ABSTRACT

This invention relates to isolated nucleic acid fragments encoding granule-bound starch synthase. The invention also relates to the construction of a recombinant DNA construct encoding all or a portion of the granule-bound starch synthase, in sense or antisense orientation, wherein expression of the recombinant DNA construct results in production of altered levels of the granule-bound starch synthase in a transformed host cell.

14 Claims, 3 Drawing Sheets

```
SEQ ID NO:02    1 ----------MAATMGSISANGSYQTNRPSALKQAPHMQF----------------QQCC
SEQ ID NO:04    1 ARAQTLFVLLQRLVAKMATLTASSNLVSRNSHVHGPTTASYESKAVAMGLRSLKQTNT
SEQ ID NO:05    1 ---------------MGSIPNYCSYQTNSVGSLKLSPHIQF---------------QQSC
                                                                                60

SEQ ID NO:02   35 NGGLRFLSKHSQS-TRSKIQVAKRRATDNGIHPKTTGHRAPIVCSAGMTIVFVATEVHPW
SEQ ID NO:04   61 HNGLRILNPVDELLNRTPIKTNAVQAMRKGPQGKNARPKGMITC--GMTFIIGTEVAPW
SEQ ID NO:05   31 NNEVMFLSM------RNKTQLAKRRATNYGTHRNSSRTPAPIVCSTGMPIIFVATEVHPW
               61                                                              120

SEQ ID NO:02   94 CKTGGLGDVVGGLPPALAAMGHRVMTIAPRYDQYKDAWDTSVLVEVNIGDTVETVRFFHC
SEQ ID NO:04  119 CKTGGLGDVIGGLPPALAGFGHRVMTIVPRYDQYKDAWDTSVVIEVKVGDRTEKVRFFHC
SEQ ID NO:05   85 CKTGGLGDVVGGLPPALAAMGHRVMTIAPRYDQYKDTWDTNVLVEVIVGDRTETVRFFHC
              121                                                              180

SEQ ID NO:02  154 YKRGVDRVFVDHPMFLEKVWGKTGAKLYGPTTGTDYRDNQLRFCLLCLAALEAPRVLNFN
SEQ ID NO:04  179 YKRGVDRVFVDHPWFLEKVWGKTGQKLYGPTTGNDYEDNQLRFSLFCQAALEAPRVLSLN
SEQ ID NO:05  145 YKRGVDRVFVDHPMFLEKVWGKTGSKLYGPTTGTDFRDNQLRFCLLCLAALEAPRVLNLN
              181                                                              240

SEQ ID NO:02  214 NSEYFSGPYGEDVVFVANDWHTAILPCYLKSMYKPNGIYKNAKVAFCIHNIAYQGRFARA
SEQ ID NO:04  239 SSKYFSGPYGEDVIFVANDWHTALIPCYLKSMYQSRGIYTNARVVFCIHNIAYQGRFAFA
SEQ ID NO:05  205 NSEYFSGPYGENVVFVANDWHTAVLPCYLKSMYKQNGIYVNAKVAFCIHNIAYQGRFPRV
              241                                                              300
```

FIG. 1A

```
SEQ ID NO:02  274 DFDLLNLPDSFLPSFDFIDGHVKPVLGRKLNWMKAGIIESDLVLTVSPHYVKELTSGPDK
SEQ ID NO:04  299 DFSLLNLPDQFKSSFDFIDGHVKPVLGRKINWLKAGLIESWFVITVSPNYAKELVSGPDK
SEQ ID NO:05  265 DFELLNLPESFMPSFDFVDGHVKPVVGRKINWMKAGITECDVVLTVSPHYVKELTSGPEK
                                                                           360

SEQ ID NO:02  334 GVELDGVLRTKPLE---IGIVNGMDVYEWDPSTDKYISAKYDATTVTEARALNKERLQAE
SEQ ID NO:04  359 GVELDNIIRKIDDDGRLVGIVNGMDVQEWNPTTDKYIAVKYDVSTVLEAKALLKEALQAE
SEQ ID NO:05  325 GVELDGVLRAKPLE---TGIVNGMDVVDWNPATDKYISVKYNATTVAEARALNKEILQAE
                                                                           420

SEQ ID NO:02  391 VGLPVDSSIPVIVFVGRLEEQKGSDILIAAIPEFVGENVQIIVLGTGKKMEEELTQLEV
SEQ ID NO:04  419 VGLPVDRNIPLIGFIGRLEEQKGSDILAEAIPQFIKQNVQLVALGTGKKQMEKQLEELEI
SEQ ID NO:05  382 VGLPVDSSIPVIVFIGRLEEQKGSDILIAAIPEFLEENVQIIVLGTGKKMEEELMLLEA
                                                                           480

SEQ ID NO:02  451 KYPNNARGIAKFNVPLAHMMFAGADFIIVPSRFEPCGLIQLQGMRYGVIPICSSTGGLVD
SEQ ID NO:04  479 SYPDKARGVAKFNVPLAHMIIAGADFILVPSRFEPCGLIQLQAMRYGSVPIVASTGGLVD
SEQ ID NO:05  442 KYPQNARGIAKFNVPLAHMMFAGANFIIVPSRFEPCGLIQLQGMRYGVIPICSSTGGLVD
                                                                           540

SEQ ID NO:02  511 TVEEGVTGFHMGSFNVECETVDPADVTAVASTVTRALKQYDTPAFHEMVQNCMAQDLSWK
SEQ ID NO:04  539 TVKEGFTGFQMGAFNVECDAVDPADVDAISKTVKRALAVYGTPAFTEIIKNCMAQDLSWK
SEQ ID NO:05  502 TVSEGVTGFHMGSFNVEFETVDPADVAAVASNVTRALKQYKTPSFHAMVQNCMAQDLSWK
                                                                           600
```

FIG. 1B

```
         ****  *** ** ***** ** *** *     ****** ** ** ***** *****
571  GPAKKWEEVLLGLGVEGSRAGIDDAEEIAPLAKENVATP  609
599  GPAKEWEEVLLSLGVPGSEPGSDG-EEIAPQAKENVATP  636
562  GPAKKWEEALLGLGVEGSQPGIEG-EEIAPLAKQNVATP  599
     601                                     639

SEQ ID NO:02
SEQ ID NO:04
SEQ ID NO:05
```

FIG. 1C

GRANULE-BOUND STARCH SYNTHASE

This application claims the benefit of U.S. Provisional Application No. 60/288,315, filed May 3, 2001, the entire contents of which are herein incorporated by reference.

FIELD OF THE INVENTION

This invention is in the field of plant molecular biology. More specifically, this invention pertains to nucleic acid fragments encoding a granule-bound starch synthase in plants and seeds.

BACKGROUND OF THE INVENTION

The molecular structure of plant starch varies from species to species or even from one developmental stage to another for a given plant and depends on the degree of polymerization and branching of the component polyglucan chains. Starch granules consist mainly of two different kinds of polymer structures: amylose which primarily consists of unbranched chains of about 1000 glucose molecules, and amylopectin which is much larger than amylose and branches every 20–25 glucose residues. Some starch granules contain phytoglycogen, a highly branched starch.

A principal enzyme that determines the extent to which these different starch forms are present in a particular starch granule is starch synthase which is involved in elongating the polyglucan chains of starch, transferring the glucose residue from ADP-glucose to the hydroxyl group in the 4-position of the terminal glucose molecule in the polymer. Starch synthases from different plant sources have different catalytic properties (e.g., rate of chain elongation, affinity for different substrates), in part accounting for the differing fine structure of starch granules observed from plant to plant.

Expectedly, starch synthase has been the focus of a number of studies. Starch synthase is localized in the plastid, where starch formation in plants occurs. Starch synthase activity has been observed bound to the starch granule ("granule-bound form") or in the supernatant of crude extracts ("soluble form"). The number of isoforms and their expression patterns vary with the plant species and the developmental stage. For example, in maize endosperm, there are at least four starch synthase isoforms, two soluble and at least two granule-bound. In potato tuber, three soluble starch synthase isoforms and at least two granule-bound isoforms have been identified. One of the three soluble isoforms in potato tuber, SSI, is expressed more in leaves than in tubers. Sequences encoding a granule-bound starch synthase from potato have been described in Hofvander et al., WO 92/11376, and Kossman et al., U.S. Pat. No. 6,130,367.

The Waxy locus encodes a granule-bound starch synthase responsible for amylose synthesis and has been cloned from several plant species (e.g., van der Leij et al. (1991) *Mol Gen Genet* 228:240–248). Genes encoding different isoforms of soluble starch synthases have been isolated as well. Certain starch synthases remain uncharacterized in detail and it is believed that additional isoforms have yet to be discovered. The chemical properties of a particular starch is ultimately determined by its structure, so that manipulation of starch structure at the molecular level, by modulating the activity of enzymes like starch synthase involved in starch biosynthesis, provides a tool for designing starch to suit a particular need, or for obtaining starch of uniform composition. For example, sorghum waxy mutants contain amylopectin exclusively, and their glutinous grains produce wine with higher quality and specific fragrance compared with those of wild-type. Accordingly, genes encoding novel isoforms of starch synthase may prove useful in producing starch structures with novel chemical properties. Disclosed herein are nucleic acid fragments encoding waxy-like starch synthase.

SUMMARY OF THE INVENTION

The present invention concerns isolated polynucleotides comprising a nucleotide sequence encoding a polypeptide having granule-bound starch synthase activity wherein the amino acid sequence of the polypeptide and amino acids 78 to 609 of the amino acid sequence of SEQ ID NO:2 have at least 90% sequence identity, or wherein the amino acid sequence of the polypeptide and amino acids 105 to 636 of the amino acid sequence of SEQ ID NO:4 have at least 80% sequence identity. It is preferred that the identity to amino acids 105 to 636 of SEQ ID NO:4 be at least 85%, it is more preferred that the identity to amino acids 105 to 636 of SEQ ID NO:4 be at least 90%, it is even more preferred that the identity to amino acids 78 to 609 of SEQ ID NO:2 or to amino acids 105 to 636 of SEQ ID NO:4 be at least 95%. The present invention also relates to isolated polynucleotides comprising the complement of the nucleotide sequence. More specifically, the present invention concerns isolated polynucleotides encoding the amino acid sequence of the following: (a) amino acids 78 to 609 of SEQ ID NO:2, (b) SEQ ID NO:2, (c) amino acids 105 to 636 of SEQ ID NO:4, (d) amino acids 18 to 636 of SEQ ID NO:4, or (e) SEQ ID NO:4, or isolated polynucleotides comprising the nucleotide sequence of SEQ ID NO:1 or SEQ ID NO:3.

In a first embodiment, the present invention concerns isolated polynucleotides comprising: (a) a first nucleotide sequence encoding a first polypeptide comprising at least 150 amino acids, wherein the amino acid sequence of the polypeptide and amino acids 78 to 609 of the amino acid sequence of SEQ ID NO:2 have at least 90% or 95% sequence identity based on the ClustalV alignment method, (b) a second nucleotide sequence encoding a second polypeptide comprising at least 250 amino acids, wherein the amino acid sequence of the second polypeptide and amino acids 105 to 636 of the amino acid sequence of SEQ ID NO:4 have at least 80%, 85%, 90% or 95% sequence identity based on the ClustalV alignment method, or (c) the complement of the first or second nucleotide sequence, wherein the complement and the first or second nucleotide sequence contain the same number of nucleotides and are 100% complementary. The first polypeptide preferably comprises amino acids 78 to 609 of the amino acid sequence of SEQ ID NO:2, or the amino acid sequence of SEQ ID NO:2, and the second polypeptide preferable comprises amino acids 105 to 636 of the amino acid sequence of SEQ ID NO:4, amino acids 18 to 636 of the amino acid sequence of SEQ ID NO:4, or the amino acid sequence of SEQ ID NO:4. The first nucleotide sequence preferably comprises the nucleotide sequence of SEQ ID NO:1, and the second nucleotide sequence preferably comprises the nucleotide sequence of SEQ ID NO:3. The isolated polynucleotides preferably encode a polypeptide having granule-bound starch synthase activity.

In a second embodiment, the present invention concerns a recombinant DNA construct comprising any of the isolated polynucleotides of the present invention operably linked to at least one regulatory sequence, and a cell, a plant, and a seed comprising the recombinant DNA construct.

In a third embodiment, the present invention relates to a vector comprising any of the isolated polynucleotides of the present invention.

In a fourth embodiment, the present invention concerns an isolated polynucleotide comprising a nucleotide sequence comprised by any of the polynucleotides of the first embodiment, wherein the nucleotide sequence contains at least 30, 40, or 60 nucleotides.

In a fifth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the present invention concerns a method for producing a transgenic plant comprising transforming a plant cell with any of the isolated polynucleotides of the present invention and regenerating a plant from the transformed plant cell. The invention is also directed to the transgenic plant produced by this method, and seed obtained from this transgenic plant.

In a seventh embodiment, the present invention concerns an isolated polypeptide comprising: (a) a first amino acid sequence comprising at least 150 amino acids, wherein the first amino acid sequence and amino acids 78 to 609 of the amino acid sequence of SEQ ID NO:2 have at least 90% or 95% identity based on the ClustalV alignment method, or (b) a second amino acid sequence comprising at least 250 amino acids, wherein the second amino acid sequence and amino acids 105 to 636 of the amino acid sequence of SEQ ID NO:4 have at least 80%, 85%, 90%, or 95% identity based on the ClustalV alignment method. The first amino acid sequence preferably comprises amino acids 78 to 609 of the amino acid sequence of SEQ ID NO:2, or the amino acid sequence of SEQ ID NO:2, and the second amino acid sequence preferably comprises amino acids 105 to 636 of SEQ ID NO:4, amino acids 18 to 636 of SEQ ID NO:4, or the amino acid sequence of SEQ ID NO:4. The polypeptide preferably is a granule-bound starch synthase.

In an eighth embodiment, the invention concerns a method for isolating a polypeptide encoded by the polynucleotide of the present invention comprising isolating the polypeptide from a cell containing a recombinant DNA construct comprising the polynucleotide operably linked to at least one regulatory sequence.

In a ninth embodiment, the present invention relates to a virus, preferably a baculovirus, comprising any of the isolated polynucleotides of the present invention or any of the recombinant DNA constructs of the present invention.

In a tenth embodiment, the invention concerns a method of selecting an isolated polynucleotide that affects the level of expression of a gene encoding a granule-bound starch synthase protein or activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of granule-bound starch synthase protein or activity in the host cell containing the isolated polynucleotide; and (d) comparing the level of granule-bound starch synthase protein or activity in the host cell containing the isolated polynucleotide with the level of granule-bound starch synthase protein or activity in the host cell that does not contain the isolated polynucleotide.

In an eleventh embodiment, the invention relates to a method of obtaining a nucleic acid fragment encoding a substantial portion of a granule-bound starch synthase protein, preferably a plant granule-bound starch synthase protein comprising the steps of: synthesizing an oligonucleotide primer comprising a nucleotide sequence of at least 30 (preferably at least 40, most preferably at least 60) contiguous nucleotides derived from a nucleotide sequence of SEQ ID NO:1 or SEQ ID NO:3 and the complement of such nucleotide sequences; and amplifying a nucleic acid fragment (preferably a cDNA inserted in a cloning vector) using the oligonucleotide primer. The amplified nucleic acid fragment preferably will encode a substantial portion of a granule-bound starch synthase protein amino acid sequence.

In a twelfth embodiment, this invention concerns a method of obtaining a nucleic acid fragment encoding all or a substantial portion of the amino acid sequence encoding a granule-bound starch synthase protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a thirteenth embodiment, this invention relates a method for positive selection of a transformed cell comprising: (a) transforming a host cell with the recombinant DNA construct of the present invention or an expression cassette of the present invention; and (b) growing the transformed host cell, preferably a plant cell, such as a monocot or a dicot, under conditions which allow expression of the granule-bound starch synthase polynucleotide in an amount sufficient to complement a null mutant to provide a positive selection means.

In a fourteenth embodiment, this invention concerns a method of altering the level of expression of a granule-bound starch synthase protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the granule-bound starch synthase protein in the transformed host cell.

BRIEF DESCRIPTION OF THE DRAWING AND SEQUENCE LISTINGS

The invention can be more fully understood from the following detailed description and the accompanying drawing and Sequence Listing which form a part of this application.

FIG. 1 (FIGS. 1A–1C) depicts the amino acid sequence alignment between the granule-bound starch synthases encoded by the following: (a) nucleotide sequence of a contig assembled from nucleotide sequences obtained from corn clones bms1.pk0008.d3, ceb5.pk0081.a8, cho1c.pk007.h4, and cs1.pk0064.c4, and PCR fragment (SEQ ID NO:2), (b) nucleotide sequence derived from soybean clone sdp2c.pk014.k6 (SEQ ID NO:4), and (c) nucleotide sequence from *Triticum aestivum* (NCBI GenBank Identifier (GI) No. 6492245; SEQ ID NO:5). Amino acids which are conserved among all and at least two sequences with an amino acid at that position are indicated with an asterisk (*). Dashes are used by the program to maximize alignment of the sequences. Amino acid positions for each sequence are indicated to the left of each line of sequence. The total number of amino acids in each sequence is indicated to the right of the last line of each sequence. The amino acid positions of the consensus sequence are indicated below the sequence alignments.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more EST, FIS or PCR fragment sequences ("Contig"), or sequences encoding the entire protein derived from an EST, an FIS, or a contig sequence ("CGS"). The sequence descriptions and Sequence Listing attached hereto comply with the rules governing nucleotide and/or amino acid sequence disclosures in patent applications as set forth in 37 C.F.R. §1.821–1.825.

TABLE 1

Granule-Bound Starch Synthase

| | | | SEQ ID NO: | |
|---|---|---|---|---|
| Plant | Clone Designation | Status | (Nucleotide) | (Amino Acid) |
| Corn | Contig of bms1.pk0008.d3 (FIS) ceb5.pk0081.a8 (FIS) cho1c.pk007.h4 (FIS) cs1.pk0064.c4 (FIS) PCR fragment sequence | CGS | 1 | 2 |
| Soybean | sdp2c.pk014.k6 (FIS) | CGS | 3 | 4 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

The problem to be solved was to identify polynucleotides that encode novel granule-bound starch synthase proteins. These polynucleotides may be used in plant cells to alter starch biosynthesis. More specifically, the polynucleotides of the instant invention may be used to create transgenic plants where the granule-bound starch synthase levels are altered with respect to non-transgenic plants which would result in plants with a certain phenotype. The present invention has solved this problem by providing polynucleotide sequences encoding deduced polypeptide sequences corresponding to novel granule-bound starch synthase proteins from corn (*Zea mays*) and soybean (*Glycine max*).

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:1 or SEQ ID NO:3, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NO:1 or SEQ ID NO:3 and the complement of such nucleotide sequences may be used to affect the expression and/or function of a granule-bound starch synthase in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. Sequence alignments and percent identity calculations were performed using the Megalign program of the LASER-GENE bioinformatics computing suite (DNASTAR Inc., Madison, Wis.). Multiple alignment of the sequences was performed using the ClustalV method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403–410; see also the explanation of the BLAST algorithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277; Ishida Y. et al. (1996) Nature Biotech. 14:745–750) and particle-accelerated or "gene gun" transformation technology (Klein et al. (1987) Nature (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

Standard recombinant DNA and molecular cloning techniques used herein are well known in the art and are described more fully in Sambrook et al. *Molecular Cloning:*

*A Laboratory Manual*; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

The present invention concerns isolated polynucleotides comprising: (a) a first nucleotide sequence encoding a first polypeptide comprising at least 150 amino acids, wherein the amino acid sequence of the polypeptide and amino acids 78 to 609 of the amino acid sequence of SEQ ID NO:2 have at least 90% or 95% sequence identity based on the ClustalV alignment method, (b) a second nucleotide sequence encoding a second polypeptide comprising at least 250 amino acids, wherein the amino acid sequence of the second polypeptide and amino acids 105 to 636 of the amino acid sequence of SEQ ID NO:4 have at least 80%, 85%, 90% or 95% sequence identity based on the ClustalV alignment method, or (c) the complement of the first or second nucleotide sequence, wherein the complement and the first or second nucleotide sequence contain the same number of nucleotides, and the nucleotide sequences of the complement and the polynucleotide have 100% complementarity. The first polypeptide preferably comprises amino acids 78 to 609 of the amino acid sequence of SEQ ID NO:2, or the amino acid sequence of SEQ ID NO:2, and the second polypeptide preferable comprises amino acids 105 to 636 of the amino acid sequence of SEQ ID NO:4, amino acids 18 to 636 of the amino acid sequence of SEQ ID NO:4, or the amino acid sequence of SEQ ID NO:4. The first nucleotide sequence preferably comprises the nucleotide sequence of SEQ ID NO:1, and the second nucleotide sequence preferably comprises the nucleotide sequence of SEQ ID NO:3. The isolated polynucleotides preferably encode a polypeptide having granule-bound starch synthase activity.

Nucleic acid fragments encoding at least a portion of several granule-bound starch synthase have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other granule-bound starch synthase proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NO:1 or SEQ ID NO:3 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the recombinant DNA constructs of the invention as described herein or isolated polynucleotides of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of granule-bound starch synthase in those cells. For example, overexpression in seed of polynucleotides encoding the novel corn and soybean granule-bound starch synthase may give rise to increased levels of amylose, and more importantly, may produce longer chain amylose. High-amylose starch is in great demand by the starch industry for its unique functional properties (Schwall et al., (2000) *Nat Biotechnol* 18:551–554).

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant isolated polynucleotide(s) (or recombinant DNA construct(s)) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA constructs described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an isolated polypeptide comprising: (a) a first amino acid sequence comprising at least 150 amino acids, wherein the first amino acid sequence and amino acids 78 to 609 of the amino acid sequence of SEQ ID NO:2 have at least 90% or 95% identity based on the ClustalV alignment method, or (b) a second amino acid sequence comprising at least 250 amino acids, wherein the second amino acid sequence and amino acids 105 to 636 of the amino acid sequence of SEQ ID NO:4 have at least 80%, 85%, 90%, or 95% identity based on the ClustalV alignment method. The first amino acid sequence preferably comprises amino acids 78 to 609 of the amino acid sequence of SEQ ID NO:2, or the amino acid sequence of SEQ ID NO:2, and the second amino acid sequence preferably comprises amino acids 105 to 636 of SEQ ID NO:4, amino acids 18 to 636 of SEQ ID NO:4, or the amino acid sequence of SEQ ID NO:4. The polypeptide preferably is a granule-bound starch synthase.

The instant polypeptides (or portions thereof) may be produced in and purified from heterologous host cells, particularly the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded granule-bound starch synthase. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several kb to several hundred kb; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn (*Zea mays*) and soybean (*Glycine max*) tissues were prepared. The characteristics of the libraries are described below.

TABLE 2 cDNA Libraries from Corn and Soybean

| Library | Tissue | Clone |
|---------|--------|-------|
| bms1 | Corn (BMS) Cell Culture 1 Day After Subculture | bms1.pk0008.d3 |
| ceb5 | Corn Embryo 30 Days After Pollination | ceb5.pk0081.a8 |
| cho1c | Corn Embryo (Alexho Synthetic High Oil) 20 Days After Pollination | cho1c.pk007.h4 |
| cs1 | Corn Leaf Sheath From 5 Week Old Plant | cs1.pk0064.c4 |
| sdp2c | Soybean Developing Pod (6–7 mm) | sdp2c.pk014.k6 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries sometimes are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding granule-bound starch synthase were identified by conducting BLAST (Basic Local Alignment Search Tool; Altschul et al. (1993) *J. Mol. Biol.* 215:403–410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Granule-bound Starch Synthase

The BLASTX search using the EST sequences from clones listed in Table 3 revealed similarity of the polypeptides encoded by the cDNAs to granule-bound starch synthase from *Antirrhinum majus* (NCBI GenBank Identifier (GI) No. 6136121) and *Triticum aestivum* (NCBI GI No. 6492245). Shown in Table 3 are the BLAST results for individual ESTs ("EST"), the sequences of the entire cDNA inserts comprising the indicated cDNA clones ("FIS"), the sequences of contigs assembled from two or more EST, FIS or PCR fragment sequences ("Contig"), or sequences encoding an entire protein derived from an FIS, a contig, or an FIS and PCR ("CGS"):

TABLE 3

BLAST Results for Sequences Encoding Polypeptides Homologous to Granule-Bound Starch Synthase

| | | BLAST Results | |
|---|---|---|---|
| Clone | Status | NCBI GI No. | pLog Score |
| Contig of<br>bms1.pk0008.d3 (FIS)<br>ceb5.pk0081.a8 (FIS)<br>cho1c.pk007.h4 (FIS)<br>cs1.pk0064.c4 (FIS) | CGS | 6492245 | >180.00 |

TABLE 3-continued

BLAST Results for Sequences Encoding Polypeptides Homologous to Granule-Bound Starch Synthase

| | | BLAST Results | |
|---|---|---|---|
| Clone | Status | NCBI GI No. | pLog Score |
| PCR fragment<br>sequence<br>sdp2c.pk014.k6 (FIS) | CGS | 6136121 | >180.00 |

FIG. 1 presents an alignment of the amino acid sequences set forth in SEQ ID NOs:2 and 4, and the *Triticum aestivum* sequence (NCBI GI No. 6492245; SEQ ID NO:5; also described in: Vrinten and Nakamura (2000) *Plant Physiol.* 122:255–263). The amino acid sequence of SEQ ID NO:2 corresponds to an open-reading frame encoded by nucleotides 266 to 2092 of the nucleic acid sequence of SEQ ID NO:1. This open-reading frame predicts a protein of 609 amino acids (SEQ ID NO:2), which is comparable in size to the wheat protein of 599 amino acids (SEQ ID NO:5). Also, in SEQ ID NO:1, the methionine codon at position 266–268 is immediately preceded, in-frame, by a stop codon at positions 263–265. SEQ ID NO:4 is a direct translation of the open-reading frame encoded by nucleotides 1 to 1908 of SEQ ID NO:3. A comparison of the amino acid sequence of SEQ ID NO:4 with the granule-bound starch synthase of corn (SEQ ID NO:2) and wheat (SEQ ID NO:5) indicates that the start methionine for the soybean protein should correspond to amino acid 18 of SEQ ID NO:4. The protein consisting of amino acids 18 to 636 of SEQ ID NO:4 contains 618 amino acids, similar to the size of the corn (609-aa) and wheat (599-aa) granule-bound starch synthases. The granule-bound starch synthase in plants is known to be a chloroplast protein, and hence the primary translation product of the corresponding mRNA should contain a transit peptide which targets the protein to the plastid. The amino-terminal end of the mature wheat chloroplast granule-bound starch synthase, GBSSII, corresponds to the serine residue at amino acid position 69 in SEQ ID NO:5, based on the protein sequencing work of Nakamura et al., (1998), *Plant Physiol.* 118:451–459. The sequence similarity between the three sequences shown in FIG. 1 begins at the processing site between the wheat chloroplast transit peptide (amino acids 1–68 of SEQ ID NO:5) and the mature wheat polypeptide (amino acids 69–599 of SEQ ID NO:5). A conserved cysteine residue appears at the carboxy-end of the transit peptide in these three sequences. By comparison to wheat, the mature polypeptide from corn corresponds to amino acids 78 to 609 of SEQ ID NO:2. Additionally, the mature polypeptide from soybean corresponds to amino acids 105 to 636 of SEQ ID NO:4. The resulting mature polypeptides from corn, soybean and wheat are 532, 532 and 531 amino acids, respectively. The KXGG consensus sequence, which is believed to be the ADP-Glucose binding site (Furukawa et al. (1990) *J. Biol. Chem.* 265:2086–2090; Furukawa et al. (1993) *J. Biol. Chem.* 268:23837–23842) is present in all three sequences of FIG. 1 at amino acid positions 122–125 of the consensus sequence.

The data in Table 4 represents a calculation of the percent identity of the amino acid sequences set forth in SEQ ID NOs:2 and 4, and the *Triticum aestivum* sequence (NCBI GI No. 6492245; SEQ ID NO:5).

TABLE 4

Percent Identity of Amino Acid Sequences Deduced From the
Nucleotide Sequences of cDNA Clones Encoding Polypeptides
Homologous to Granule-Bound Starch Synthase

| SEQ ID NO. | Percent Identity to NCBI GI No. 6492245 |
| --- | --- |
| 2 | 84.1 |
| 4 | 65.8 |

Sequence alignments and percent identity calculations were performed using the Megalign program of the LASERGENE bioinformatics computing suite (DNASTAR Inc., Madison, Wis.). Multiple alignment of the sequences was performed using the ClustalV method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a granule-bound starch synthase. These sequences represent a new corn sequence and the first soybean sequence encoding granule-bound starch synthase known to Applicant.

Example 4

Expression of Recombinant DNA Constructs in Monocot Cells

A recombinant DNA construct comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptide, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium.

These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Starch synthase activities of the granule-bound and soluble fractions of plant tissues can be assayed by the incorporation of [$^{14}$C]ADP-Glucose according to the method of Singletary et al., (1997), *Plant Physiol.* 113:293–304, with minor modifications as described by Nakamura et al., (1998), *Plant Physiol.* 118:451–459. Amylose content of starch granules can be measured by the method of Yamamori et al., (1992), *Euphytica* 64:215–219.

Example 5

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/mL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Starch synthase activities of the granule-bound and soluble fractions of plant tissues can be assayed by the incorporation of [$^{14}$C]ADP-Glucose according to the method of Singletary et al., (1997), *Plant Physiol.* 113:293–304, with minor modifications as described by Nakamura et al., (1998), *Plant Physiol.* 118:451–459. Amylose content of starch granules can be measured by the method of Yamamori et al., (1992), *Euphytica* 64:215–219.

Example 6

Expression of Recombinant DNA Constructs in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having granule-bound starch synthase activity, wherein the amino acid sequence of the polypeptide and amino acids 78 to 609 of the amino acid sequence of SEQ ID NO:2 have at least 90% sequence identity based on the ClustalV alignment method with pairwise alignment default parameters of KTUPLE=1, GAP PENALTY=3, WINDOW=5 and DIAGONALS SAVED=5, or
   (b) the complement of the nucleotide sequence of (a), wherein the complement and the nucleotide sequence of (a) contain the same number of nucleotides and are 100% complementary.

2. The polynucleotide of claim 1, wherein the amino acid sequence of the polypeptide and the amino acid sequence of SEQ ID NO:2 have at least 90% sequence identity based on the ClustalV alignment method with the pairwise alignment default parameters.

3. The polynucleotide of claim 1, wherein the amino acid sequence of the polypeptide and amino acids 78 to 609 of the amino acid sequence of SEQ ID NO:2 have at least 95% sequence identity based on the ClustalV alignment method with the pairwise alignment default parameters.

4. The polynucleotide of claim 1, wherein the amino acid sequence of the polypeptide comprises amino acid 78 to 609 of the amino acid sequence of SEQ ID NO:2.

5. The polynucleotide of claim 1, wherein the amino acid sequence of the polypeptide comprises the amino acid sequence of SEQ ID NO:2.

6. The polynucleotide of claim 1 wherein the nucleotide sequence comprises the nucleotide sequence of SEQ ID NO:1.

7. A vector comprising the polynucleotide of claim 1.

8. A recombinant DNA construct comprising the polynucleotide of claim 1 operably linked to at least one regulatory sequence.

9. A method for transforming a cell, comprising transforming a cell with the polynucleotide of claim 1.

10. A cell comprising the recombinant DNA construct of claim 8.

11. A method for producing a transgenic plant comprising transforming a plant cell with the polynucleotide of claim 1 and regenerating a transgenic plant from the transformed plant cell.

12. A plant comprising the recombinant DNA construct of claim 8.

13. A seed comprising the recombinant DNA construct of claim 8.

14. A method for isolating polypeptide encoded by the polynucleotide of claim 1 comprising isolating the polypeptide from a cell, wherein the cell comprises a recombinant DNA construct comprising said polynucleotide operably linked to at least one regulatory sequence.

* * * * *

UNITED STATES PATENT AND TRADEMARK OFFICE
CERTIFICATE OF CORRECTION

PATENT NO. : 6,930,226 B2 Page 1 of 1
APPLICATION NO. : 10/138075
DATED : August 16, 2005
INVENTOR(S) : Karen E. Broglie et al.

It is certified that error appears in the above-identified patent and that said Letters Patent is hereby corrected as shown below:

Title page, Item [56] OTHER PUBLICATIONS section, Column 1, 2nd Reference, please delete "1996" and insert therefor --1998--.

Title page, Item [56] OTHER PUBLICATIONS section, Column 2, Last Reference, after the word 'Mutants', delete "PF" and insert therefor --of--.

Colum 4, Claims section, Claim 4, line 53, before the number '78', delete the word "acid" and insert therefor --acids--.

Signed and Sealed this

Thirtieth Day of January, 2007

JON W. DUDAS
*Director of the United States Patent and Trademark Office*

SEQUENCE LISTING

<160> NUMBER OF SEQ ID NOS: 5

<210> SEQ ID NO 1
<211> LENGTH: 2399
<212> TYPE: DNA
<213> ORGANISM: Zea mays

<400> SEQUENCE: 1

| | | | | | |
|---|---|---|---|---|---|
| gtgcagcgat | tgtgtggcgc | ccgtgcgcta | gccactaggc | ggggcgcacg | ccgcctgtca | 60 |
| cgtgggcgat | atttttcctg | gccctcggcg | gtcggcgcgc | tgcgtcgccg | cttgcttcct | 120 |
| cctctacttg | agtgccgagt | cgcctccgcg | ctctgcagtc | ccccgacccg | gagccaaagc | 180 |
| caacaaacag | ccgctccgcc | ttcttccgcg | gctgcagcca | gcgcgaggta | cctggctggc | 240 |
| attttgcatt | tgaggtcatc | attgaatggc | tgcaacgatg | ggttcaatat | ctgccaatgg | 300 |
| ttcttaccaa | acaaataggc | ccagtgcact | aaagcaggca | cctcacatgc | aattccaaca | 360 |
| atgttgcaac | ggtggactta | ggttcttaag | caagcattcc | caatccacgc | gaagtaagat | 420 |
| acaggtggct | aaaagaagag | ctacagataa | tggaattcat | ccaaagacta | cgggacatcg | 480 |
| ggcacctatt | gtatgttctg | ctgggatgac | tattgtattt | gttgcaactg | aagtgcaccc | 540 |
| atggtgcaaa | actggtggcc | tcggtgatgt | tgtaggagga | ctgcccccag | ctttggctgc | 600 |
| tatgggacac | cgtgtcatga | caatagctcc | tcgttatgat | caatacaagg | atgcatggga | 660 |
| tacaagtgtc | cttgttgagg | taaatattgg | tgacacggta | gaaactgttc | gcttcttcca | 720 |
| ctgctacaaa | agaggagttg | atcgtgtttt | tgttgatcat | cctatgtttc | ttgaaaaggt | 780 |
| atggggcaag | actggagcaa | aattgtatgg | tcctactact | ggaactgact | atcgagataa | 840 |
| ccagttgagg | ttctgccttt | tgtgccttgc | tgctttggag | gctccaagag | ttctcaattt | 900 |
| caacaattct | gaatatttct | ctggaccata | tggggaagat | gttgtcttcg | tagccaatga | 960 |
| ttggcacact | gctatttgc | catgttatct | gaagagcatg | tataagccaa | atggaattta | 1020 |

-continued

```
taaaaatgct aaggttgctt tctgcataca taatattgcc tatcaaggta gatttgccag    1080
agcagacttc gatcttctta atctacctga cagtttcttg ccatcatttg attttattga    1140
tggacatgtt aagcctgttc tagggagaaa gcttaactgg atgaaggcag ggatcattga    1200
gagtgatctg gttctaacag tcagtccaca ttatgtcaag gaactcactt ctggcccaga    1260
taagggtgtt gagttggatg gtgtccttcg cacaaagcct ctagaaattg aatcgtaaa     1320 tggcatggat gtttatgaat gggatccttc aacagataag tacatcagcg cgaaatatga    1380
tgcaacaacg gtaactgaag caagggctct caataaagag aggttgcaag ccgaagtcgg    1440
attgcctgtg gactcgagca tccctgttat agttttcgtc gggcgtctcg aagaacagaa    1500
agggtccgac atactcattg cagccattcc agagttcgtg ggcgagaatg tccagataat    1560
cgttcttggc acgggaaaga agaagatgga ggaggaacta acgcagctgg aagtgaaata    1620
tccaaacaac gctagaggca tagcgaaatt caatgttcca ttggcacaca tgatgtttgc    1680
cggggctgac ttcattatcg tcccaagcag gtttgagcca tgtggtctca ttcagctgca    1740
agggatgaga tatggagtga ttcccatctg ttcatccact ggaggacttg tcgacacggt    1800
tgaggagggc gtcaccggat ccacatgggt tctttcaat gtcgagtgtg aaactgtaga     1860
cccagctgac gtgacagcag tagcgtcaac cgtcacgcga gccctgaagc agtacgacac    1920
cccggcgttc catgagatgg ttcagaactg catggcgcaa gacctgtcct ggaaggggcc    1980
tgcgaagaag tgggaggagg tgcttctggg ccttggagtc gagggagtc gagctggcat     2040 cgacgacgca gaggagatcg ccccacttgc caaggaaaac gtagccactc cgtgagggct    2100
tggtggtgcc tcggacgagg aaacacgcgt tggtgatagg aagcgtcttc taggatcctc    2160
ctgggcggcc ttgtgctgg tggagtgagg tgtccagtca gacacggttt cgcctctact     2220
actagtctac tactactcct cattgtaata taatccttgg cattctagta aatgccatgc    2280
ctgctctaat aggtcctgtt ctattgctag accttttgcc tcctaaatag acgatgtact    2340
gcgcttgtaa caagaacctc actttcgtgt caagtaatat caacaggttt cataatggt     2399
```

<210> SEQ ID NO 2
<211> LENGTH: 609
<212> TYPE: PRT
<213> ORGANISM: Zea mays

<400> SEQUENCE: 2

```
Met Ala Ala Thr Met Gly Ser Ile Ser Ala Asn Gly Ser Tyr Gln Thr
 1               5                  10                  15

Asn Arg Pro Ser Ala Leu Lys Gln Ala Pro His Met Gln Phe Gln Gln
             20                  25                  30

Cys Cys Asn Gly Gly Leu Arg Phe Leu Ser Lys His Ser Gln Ser Thr
         35                  40                  45

Arg Ser Lys Ile Gln Val Ala Lys Arg Ala Thr Asp Asn Gly Ile
     50                  55                  60

His Pro Lys Thr Thr Gly His Arg Ala Pro Ile Val Cys Ser Ala Gly
 65                  70                  75                  80

Met Thr Ile Val Phe Val Ala Thr Glu Val His Pro Trp Cys Lys Thr
                 85                  90                  95

Gly Gly Leu Gly Asp Val Val Gly Gly Leu Pro Pro Ala Leu Ala Ala
            100                 105                 110

Met Gly His Arg Val Met Thr Ile Ala Pro Arg Tyr Asp Gln Tyr Lys
        115                 120                 125

Asp Ala Trp Asp Thr Ser Val Leu Val Glu Val Asn Ile Gly Asp Thr
```

-continued

```
            130                 135                 140
Val Glu Thr Val Arg Phe His Cys Tyr Lys Arg Gly Val Asp Arg
145                 150                 155                 160
Val Phe Val Asp His Pro Met Phe Leu Glu Lys Val Trp Gly Lys Thr
                165                 170                 175
Gly Ala Lys Leu Tyr Gly Pro Thr Thr Gly Thr Asp Tyr Arg Asp Asn
                180                 185                 190
Gln Leu Arg Phe Cys Leu Leu Cys Leu Ala Ala Leu Glu Ala Pro Arg
                195                 200                 205
Val Leu Asn Phe Asn Asn Ser Glu Tyr Phe Ser Gly Pro Tyr Gly Glu
            210                 215                 220
Asp Val Val Phe Val Ala Asn Asp Trp His Thr Ala Ile Leu Pro Cys
225                 230                 235                 240
Tyr Leu Lys Ser Met Tyr Lys Pro Asn Gly Ile Tyr Lys Asn Ala Lys
                245                 250                 255
Val Ala Phe Cys Ile His Asn Ile Ala Tyr Gln Gly Arg Phe Ala Arg
                260                 265                 270
Ala Asp Phe Asp Leu Leu Asn Leu Pro Asp Ser Phe Leu Pro Ser Phe
                275                 280                 285
Asp Phe Ile Asp Gly His Val Lys Pro Val Leu Gly Arg Lys Leu Asn
                290                 295                 300
Trp Met Lys Ala Gly Ile Ile Glu Ser Asp Leu Val Leu Thr Val Ser
305                 310                 315                 320
Pro His Tyr Val Lys Glu Leu Thr Ser Gly Pro Asp Lys Gly Val Glu
                325                 330                 335
Leu Asp Gly Val Leu Arg Thr Lys Pro Leu Glu Ile Gly Ile Val Asn
                340                 345                 350
Gly Met Asp Val Tyr Glu Trp Asp Pro Ser Thr Asp Lys Tyr Ile Ser
                355                 360                 365
Ala Lys Tyr Asp Ala Thr Thr Val Thr Glu Ala Arg Ala Leu Asn Lys
                370                 375                 380
Glu Arg Leu Gln Ala Glu Val Gly Leu Pro Val Asp Ser Ser Ile Pro
385                 390                 395                 400
Val Ile Val Phe Val Gly Arg Leu Glu Glu Gln Lys Gly Ser Asp Ile
                405                 410                 415
Leu Ile Ala Ala Ile Pro Glu Phe Val Gly Glu Asn Val Gln Ile Ile
                420                 425                 430
Val Leu Gly Thr Gly Lys Lys Lys Met Glu Glu Glu Leu Thr Gln Leu
                435                 440                 445
Glu Val Lys Tyr Pro Asn Asn Ala Arg Gly Ile Ala Lys Phe Asn Val
                450                 455                 460
Pro Leu Ala His Met Met Phe Ala Gly Ala Asp Phe Ile Ile Val Pro
465                 470                 475                 480
Ser Arg Phe Glu Pro Cys Gly Leu Ile Gln Leu Gln Gly Met Arg Tyr
                485                 490                 495
Gly Val Ile Pro Ile Cys Ser Ser Thr Gly Gly Leu Val Asp Thr Val
                500                 505                 510
Glu Glu Gly Val Thr Gly Phe His Met Gly Ser Phe Asn Val Glu Cys
                515                 520                 525
Glu Thr Val Asp Pro Ala Asp Val Thr Ala Val Ala Ser Thr Val Thr
                530                 535                 540
Arg Ala Leu Lys Gln Tyr Asp Thr Pro Ala Phe His Glu Met Val Gln
545                 550                 555                 560
```

| | | |
|---|---|---|
| Asn Cys Met Ala Gln Asp Leu Ser Trp Lys Gly Pro Ala Lys Lys Trp | | |
| 565 570 575 | | |
| Glu Glu Val Leu Leu Gly Leu Gly Val Glu Gly Ser Arg Ala Gly Ile | | |
| 580 585 590 | | |
| Asp Asp Ala Glu Glu Ile Ala Pro Leu Ala Lys Glu Asn Val Ala Thr | | |
| 595 600 605 | | |
| Pro | | |

<210> SEQ ID NO 3
<211> LENGTH: 2179
<212> TYPE: DNA
<213> ORGANISM: Glycine max

<400> SEQUENCE: 3

| | |
|---|---|
| gcacgagccc aaactctctt tgttgtgctg cttcagcgtc tggtagcaaa gatggcgaca | 60 |
| ttgactgctt caagtaactt agtctctaga aattctcatg tccaccatgg accaacaact | 120 |
| gcttcatatg agtctaaagc agtagcaatg ggacttagat ctctgaagca gacaaatact | 180 |
| cataatggac taagaatttt gaacccggtg gatgagctac ttaacagaac cccaattaaa | 240 |
| accaatgcag tgcaagctat gaggaaggga cctcaaggca agaatgccag gcctaaaggc | 300 |
| atgatcacat gtggcatgac tttcataatt ataggaaccg aggtggctcc atggtgcaaa | 360 |
| actggtgggt tgggagatgt tcttggaggt ctaccaccgg cattggcagg ttttgggcat | 420 |
| cgagtaatga ctattgtgcc gcgctatgac cagtacaaag atgcatggga tacaagtgtt | 480 |
| gtaattgagg tgaaagtagg agatagaaca gaaaaggttc gcttcttcca ttgttataag | 540 |
| aggggagttg atcgtgtctt tgtggatcac ccttggtttc ttgaaaaggt atggggggaaa | 600 |
| actggacaaa aactttatgg accaactact ggaaatgatt acgaagacaa ccaactgcgt | 660 |
| tttagcctct tttgccaggc tgctttggaa gccccaaggg ttctgagtct taattccagt | 720 |
| aaatatttct ctggaccata tggtgaagat gtcatttttg ttgccaatga ttggcacact | 780 |
| gcccttatcc cctgctactt gaaaagtatg taccagtcaa ggggcatcta tacgaatgcc | 840 |
| cgggttgttt tttgtatcca acacattgct taccaaggaa gatttgcatt cgccgacttc | 900 |
| tcacttctaa atctcccaga ccaatttaag agctcctttg actttattga tgggcatgtt | 960 |
| aaaccagtgg ttgaaggaa atcaattgg ttgaaagctg gacttataga atcatggttt | 1020 |
| gtgataaccg ttagtccaaa ctatgctaaa gaactggtgt caggtccaga caaaggagtg | 1080 |
| gaattggaca acatcattcg caaaattgat gatgatggtc gtttggttgg aattgtgaat | 1140 |
| ggcatggatg ttcaggagtg gaatccaacc actgacaaat atatagctgt caaatatgat | 1200 |
| gtttcaacag tattggaagc aaaggctctt ctgaaagaag ccctccaagc agaagttgga | 1260 |
| ttgccagtcg acagaaatat tcctctcatt ggtttcattg gtaggcttga agagcaaaaa | 1320 |
| ggttctgata ttccttgcaga agccattccc caatttatca agcagaatgt tcagttggta | 1380 |
| gccctaggaa caggaaaaaa acaaatggaa aagcagcttg aggaacttga aatatcatac | 1440 |
| cctgataagg ccagaggagt ggcaaaattc aatgttcccc tagcccacat gataatagct | 1500 |
| ggagctgatt ttatattggt tcctagcaga tttgagcctt gtggtctcat tcagttacaa | 1560 |
| gctatgcgct atggatctgt accaattgtt gcctcaacag gtggattagt tgacactgtc | 1620 |
| aaagaaggct tcactggatt tcagatgggt gccttcaatg ttgaatgtga tgctgtggat | 1680 |
| ccggctgatg tggatgctat atcaaagact gtcaaagggg cccttgcagt ctatggaact | 1740 |
| ccagctttta cagaaattat caagaactgc atggctcaag atctttcatg gaaggggcct | 1800 |

-continued

```
gctaaggagt gggaggaagt gctgctaagc ttgggagttc ctggcagtga acctggaagt    1860
gatggagaag aaattgctcc acaggcaaag gaaaatgtgg caacaccata ataataagaa    1920
caaagatgtg agggaagcct ctcctagtct gagtctcgtg aagttctccc agcccttgc     1980 ttgttattaa tattatgttt tatatccttc ttccaaattt ttgttttctt ctaaatagat    2040
tatagaaatg tacatggaca cggaaattac actattcgaa tcagtgtaat gagtgcaggt    2100
ctttcaagat tagcataaat taaagcgttt cttaatagtc taaaaaaaaa aaaaaaaaa     2160 aaaaaaaaaa aaaaaaaa                                                  2179
```

<210> SEQ ID NO 4
<211> LENGTH: 636
<212> TYPE: PRT
<213> ORGANISM: Glycine max

<400> SEQUENCE: 4

```
Ala Arg Ala Gln Thr Leu Phe Val Val Leu Leu Gln Arg Leu Val Ala
  1               5                  10                  15

Lys Met Ala Thr Leu Thr Ala Ser Ser Asn Leu Val Ser Arg Asn Ser
             20                  25                  30

His Val His Gly Pro Thr Thr Ala Ser Tyr Glu Ser Lys Ala Val
         35                  40                  45

Ala Met Gly Leu Arg Ser Leu Lys Gln Thr Asn Thr His Asn Gly Leu
     50                  55                  60

Arg Ile Leu Asn Pro Val Asp Glu Leu Leu Asn Arg Thr Pro Ile Lys
 65                  70                  75                  80

Thr Asn Ala Val Gln Ala Met Arg Lys Gly Pro Gln Gly Lys Asn Ala
                 85                  90                  95

Arg Pro Lys Gly Met Ile Thr Cys Gly Met Thr Phe Ile Ile Ile Gly
            100                 105                 110

Thr Glu Val Ala Pro Trp Cys Lys Thr Gly Gly Leu Gly Asp Val Leu
        115                 120                 125

Gly Gly Leu Pro Pro Ala Leu Ala Gly Phe Gly His Arg Val Met Thr
    130                 135                 140

Ile Val Pro Arg Tyr Asp Gln Tyr Lys Asp Ala Trp Asp Thr Ser Val
145                 150                 155                 160

Val Ile Glu Val Lys Val Gly Asp Arg Thr Glu Lys Val Arg Phe Phe
                165                 170                 175

His Cys Tyr Lys Arg Gly Val Asp Arg Val Phe Val Asp His Pro Trp
            180                 185                 190

Phe Leu Glu Lys Val Trp Gly Lys Thr Gly Gln Lys Leu Tyr Gly Pro
        195                 200                 205

Thr Thr Gly Asn Asp Tyr Glu Asp Asn Gln Leu Arg Phe Ser Leu Phe
    210                 215                 220

Cys Gln Ala Ala Leu Glu Ala Pro Arg Val Leu Ser Leu Asn Ser Ser
225                 230                 235                 240

Lys Tyr Phe Ser Gly Pro Tyr Gly Glu Asp Val Ile Phe Val Ala Asn
                245                 250                 255

Asp Trp His Thr Ala Leu Ile Pro Cys Tyr Leu Lys Ser Met Tyr Gln
            260                 265                 270

Ser Arg Gly Ile Tyr Thr Asn Ala Arg Val Val Phe Cys Ile His Asn
        275                 280                 285

Ile Ala Tyr Gln Gly Arg Phe Ala Phe Ala Asp Phe Ser Leu Leu Asn
    290                 295                 300
```

```
Leu Pro Asp Gln Phe Lys Ser Ser Phe Asp Phe Ile Asp Gly His Val
305                 310                 315                 320

Lys Pro Val Val Gly Arg Lys Ile Asn Trp Leu Lys Ala Gly Leu Ile
            325                 330                 335

Glu Ser Trp Phe Val Ile Thr Val Ser Pro Asn Tyr Ala Lys Glu Leu
                340                 345                 350

Val Ser Gly Pro Asp Lys Gly Val Glu Leu Asp Asn Ile Ile Arg Lys
        355                 360                 365

Ile Asp Asp Asp Gly Arg Leu Val Gly Ile Val Asn Gly Met Asp Val
370                 375                 380

Gln Glu Trp Asn Pro Thr Thr Asp Lys Tyr Ile Ala Val Lys Tyr Asp
385                 390                 395                 400

Val Ser Thr Val Leu Glu Ala Lys Ala Leu Leu Lys Glu Ala Leu Gln
                405                 410                 415

Ala Glu Val Gly Leu Pro Val Asp Arg Asn Ile Pro Leu Ile Gly Phe
            420                 425                 430

Ile Gly Arg Leu Glu Glu Gln Lys Gly Ser Asp Ile Leu Ala Glu Ala
        435                 440                 445

Ile Pro Gln Phe Ile Lys Gln Asn Val Gln Leu Val Ala Leu Gly Thr
450                 455                 460

Gly Lys Lys Gln Met Glu Lys Gln Leu Glu Leu Glu Ile Ser Tyr
465                 470                 475                 480

Pro Asp Lys Ala Arg Gly Val Ala Lys Phe Asn Val Pro Leu Ala His
                485                 490                 495

Met Ile Ile Ala Gly Ala Asp Phe Ile Leu Val Pro Ser Arg Phe Glu
            500                 505                 510

Pro Cys Gly Leu Ile Gln Leu Gln Ala Met Arg Tyr Gly Ser Val Pro
        515                 520                 525

Ile Val Ala Ser Thr Gly Gly Leu Val Asp Thr Val Lys Glu Gly Phe
530                 535                 540

Thr Gly Phe Gln Met Gly Ala Phe Asn Val Glu Cys Asp Ala Val Asp
545                 550                 555                 560

Pro Ala Asp Val Asp Ala Ile Ser Lys Thr Val Lys Arg Ala Leu Ala
                565                 570                 575

Val Tyr Gly Thr Pro Ala Phe Thr Glu Ile Ile Lys Asn Cys Met Ala
            580                 585                 590

Gln Asp Leu Ser Trp Lys Gly Pro Ala Lys Glu Trp Glu Glu Val Leu
        595                 600                 605

Leu Ser Leu Gly Val Pro Gly Ser Glu Pro Gly Ser Asp Gly Glu Glu
610                 615                 620

Ile Ala Pro Gln Ala Lys Glu Asn Val Ala Thr Pro
625                 630                 635

<210> SEQ ID NO 5
<211> LENGTH: 599
<212> TYPE: PRT
<213> ORGANISM: Triticum aestivum

<400> SEQUENCE: 5

Met Gly Ser Ile Pro Asn Tyr Cys Ser Tyr Gln Thr Asn Ser Val Gly
1               5                   10                  15

Ser Leu Lys Leu Ser Pro His Ile Gln Phe Gln Gln Ser Cys Asn Asn
            20                  25                  30

Glu Val Met Phe Leu Ser Met Arg Asn Lys Thr Gln Leu Ala Lys Arg
```

-continued

```
                35                  40                  45
Arg Ala Thr Asn Tyr Gly Thr His Arg Asn Ser Ser Arg Thr Pro Ala
         50                  55                  60
Pro Ile Val Cys Ser Thr Gly Met Pro Ile Ile Phe Val Ala Thr Glu
 65                  70                  75                  80
Val His Pro Trp Cys Lys Thr Gly Leu Gly Asp Val Val Gly Gly
                 85                  90                  95
Leu Pro Pro Ala Leu Ala Ala Met Gly His Arg Val Met Thr Ile Ala
                100                 105                 110
Pro Arg Tyr Asp Gln Tyr Lys Asp Thr Trp Asp Thr Asn Val Leu Val
                115                 120                 125
Glu Val Ile Val Gly Asp Arg Thr Glu Thr Val Arg Phe Phe His Cys
130                 135                 140
Tyr Lys Arg Gly Val Asp Arg Val Phe Val Asp His Pro Met Phe Leu
145                 150                 155                 160
Glu Lys Val Trp Gly Lys Thr Gly Ser Lys Leu Tyr Gly Pro Thr Thr
                165                 170                 175
Gly Thr Asp Phe Arg Asp Asn Gln Leu Arg Phe Cys Leu Leu Cys Leu
                180                 185                 190
Ala Ala Leu Glu Ala Pro Arg Val Leu Asn Leu Asn Asn Ser Glu Tyr
                195                 200                 205
Phe Ser Gly Pro Tyr Gly Glu Asn Val Val Phe Val Ala Asn Asp Trp
                210                 215                 220
His Thr Ala Val Leu Pro Cys Tyr Leu Lys Ser Met Tyr Lys Gln Asn
225                 230                 235                 240
Gly Ile Tyr Val Asn Ala Lys Val Ala Phe Cys Ile His Asn Ile Ala
                245                 250                 255
Tyr Gln Gly Arg Phe Pro Arg Val Asp Phe Glu Leu Leu Asn Leu Pro
                260                 265                 270
Glu Ser Phe Met Pro Ser Phe Asp Phe Val Asp Gly His Val Lys Pro
                275                 280                 285
Val Val Gly Arg Lys Ile Asn Trp Met Lys Ala Gly Ile Thr Glu Cys
                290                 295                 300
Asp Val Val Leu Thr Val Ser Pro His Tyr Val Lys Glu Leu Thr Ser
305                 310                 315                 320
Gly Pro Glu Lys Gly Val Glu Leu Asp Gly Val Leu Arg Ala Lys Pro
                325                 330                 335
Leu Glu Thr Gly Ile Val Asn Gly Met Asp Val Val Asp Trp Asn Pro
                340                 345                 350
Ala Thr Asp Lys Tyr Ile Ser Val Lys Tyr Asn Ala Thr Thr Val Ala
                355                 360                 365
Glu Ala Arg Ala Leu Asn Lys Glu Ile Leu Gln Ala Glu Val Gly Leu
                370                 375                 380
Pro Val Asp Ser Ser Ile Pro Val Ile Val Phe Ile Gly Arg Leu Glu
385                 390                 395                 400
Glu Gln Lys Gly Ser Asp Ile Leu Ile Ala Ala Ile Pro Glu Phe Leu
                405                 410                 415
Glu Glu Asn Val Gln Ile Ile Val Leu Gly Thr Gly Lys Lys Lys Met
                420                 425                 430
Glu Glu Glu Leu Met Leu Leu Glu Ala Lys Tyr Pro Gln Asn Ala Arg
                435                 440                 445
Gly Ile Ala Lys Phe Asn Val Pro Leu Ala His Met Met Phe Ala Gly
                455                 460
```

-continued

```
Ala Asn Phe Ile Ile Val Pro Ser Arg Phe Glu Pro Cys Gly Leu Ile
465                 470                 475                 480

Gln Leu Gln Gly Met Arg Tyr Gly Val Ile Pro Ile Cys Ser Ser Thr
            485                 490                 495

Gly Gly Leu Val Asp Thr Val Ser Glu Gly Val Thr Gly Phe His Met
            500                 505                 510

Gly Ser Phe Asn Val Glu Phe Glu Thr Val Asp Pro Ala Asp Val Ala
        515                 520                 525

Ala Val Ala Ser Asn Val Thr Arg Ala Leu Lys Gln Tyr Lys Thr Pro
    530                 535                 540

Ser Phe His Ala Met Val Gln Asn Cys Met Ala Gln Asp Leu Ser Trp
545                 550                 555                 560

Lys Gly Pro Ala Lys Lys Trp Glu Glu Ala Leu Leu Gly Leu Gly Val
            565                 570                 575

Glu Gly Ser Gln Pro Gly Ile Glu Gly Glu Glu Ile Ala Pro Leu Ala
            580                 585                 590

Lys Gln Asn Val Ala Thr Pro
            595
```